United States Patent
Min et al.

(10) Patent No.: US 7,396,452 B2
(45) Date of Patent: Jul. 8, 2008

(54) APPARATUS FOR DETERMINING FLOW RATES OF BIOLOGICAL FLUIDS

(75) Inventors: Kyungyoon Min, Gurnee, IL (US); Richard I. Brown, Northbrook, IL (US)

(73) Assignee: Fenwal, Inc., Lake Zurich, IL (US)

( * ) Notice: Subject to any disclaimer, the term of this patent is extended or adjusted under 35 U.S.C. 154(b) by 68 days.

(21) Appl. No.: 11/427,402

(22) Filed: Jun. 29, 2006

(65) Prior Publication Data

US 2007/0000848 A1    Jan. 4, 2007

Related U.S. Application Data

(62) Division of application No. 10/826,086, filed on Apr. 16, 2004, now Pat. No. 7,087,177.

(51) Int. Cl.
| | |
|---|---|
| B01D 21/30 | (2006.01) |
| B01D 21/26 | (2006.01) |
| G01F 1/00 | (2006.01) |
| B01D 21/32 | (2006.01) |
| B04B 11/00 | (2006.01) |

(52) U.S. Cl. ............. 210/143; 210/85; 210/87; 210/97; 210/134; 210/138; 210/782; 210/787; 210/789; 494/1; 494/3; 494/5; 494/6; 494/10; 494/17; 73/861; 73/861.04

(58) Field of Classification Search ............ 210/782, 210/787, 789, 85, 87, 97, 134, 138, 143, 210/145; 494/1, 3, 5, 6, 10, 17, 37; 73/861, 73/861.04, 861.77

See application file for complete search history.

(56) References Cited

U.S. PATENT DOCUMENTS

| | | | |
|---|---|---|---|
| 4,185,629 A | 1/1980 | Cullis et al. | |
| 4,191,182 A | 3/1980 | Popovich et al. | |
| 4,269,718 A | 5/1981 | Persidsky | |
| 4,321,919 A | 3/1982 | Edelson | |
| 4,375,415 A | 3/1983 | Lavender | |
| RE31,688 E | 9/1984 | Popovich et al. | |
| 4,631,130 A | 12/1986 | Watanabe | |

(Continued)

FOREIGN PATENT DOCUMENTS

EP    0 834 329 A1    4/1998

*Primary Examiner*—John Kim
(74) *Attorney, Agent, or Firm*—Cook, Alex, McFarron, Manzo, Cummings & Mehler, Ltd.

(57) ABSTRACT

An apparatus comprises an inlet to convey a first fluid comprising first and second components having different density into a rotating chamber such that an interface forms between at least portions of such components at a first location. At least one outlet removes at least one of the first and second components. A controller is adapted to introduce the first fluid and is operable to move the interface from the first location to a second location and to move the interface from the second location in a direction toward the first location and to return the interface to the second location. The controller is operable to determine a flow rate of the first or second component based, at least in part, on the time interval between when the interface moves from and returns to the second location. At least one sensing assembly is adapted to sense the location of the interface.

10 Claims, 4 Drawing Sheets

U.S. PATENT DOCUMENTS

| | | |
|---|---|---|
| 4,747,952 A | 5/1988 | Nakano et al. |
| 4,755,300 A | 7/1988 | Fischel et al. |
| 4,769,001 A | 9/1988 | Prince |
| 4,789,482 A | 12/1988 | DiLeo et al. |
| 4,808,307 A | 2/1989 | Fischel et al. |
| 4,898,675 A | 2/1990 | Lavender |
| 4,944,883 A | 7/1990 | Schoendorfer et al. |
| 4,980,068 A | 12/1990 | Lavender |
| 5,061,381 A | 10/1991 | Burd |
| 5,178,603 A | 1/1993 | Prince |
| 5,194,145 A | 3/1993 | Schoendorfer |
| 5,234,608 A | 8/1993 | Duff |
| 5,242,384 A | 9/1993 | Robinson et al. |
| 5,281,342 A | 1/1994 | Biesel et al. |
| 5,318,512 A | 6/1994 | Neumann |
| 5,348,533 A | 9/1994 | Papillon et al. |
| 5,372,709 A | 12/1994 | Hood |
| 5,376,263 A | 12/1994 | Fischel |
| 5,421,812 A | 6/1995 | Langley et al. |
| 5,437,624 A | 8/1995 | Langley |
| 5,494,592 A | 2/1996 | Latham, Jr. et al. |
| 5,516,431 A | 5/1996 | Kawamura et al. |
| 5,607,579 A | 3/1997 | Latham, Jr. et al. |
| 5,607,830 A | 3/1997 | Biesel et al. |
| 5,653,681 A | 8/1997 | Ellingboe |
| 5,681,273 A | 10/1997 | Brown |
| 5,704,888 A | 1/1998 | Hlavinka et al. |
| 5,704,889 A | 1/1998 | Hlavinka et al. |
| 5,730,883 A | 3/1998 | Brown |
| 5,738,792 A | 4/1998 | Schoendorfer |
| 5,762,791 A | 6/1998 | Deniega et al. |
| 5,876,321 A | 3/1999 | Hlavinka et al. |
| 5,879,280 A | 3/1999 | Hlavinka et al. |
| 6,013,184 A | 1/2000 | Fukuda et al. |
| 6,022,306 A | 2/2000 | Dumont et al. |
| 6,059,979 A | 5/2000 | Brown |
| 6,080,322 A | 6/2000 | Deniega et al. |
| 6,083,187 A | 7/2000 | Nakayama et al. |
| 6,200,287 B1 | 3/2001 | Keller et al. |
| 6,207,063 B1 | 3/2001 | Brown |
| 6,251,284 B1 | 6/2001 | Bischof et al. |
| 6,315,955 B1 | 11/2001 | Klein |
| 6,451,203 B2 | 9/2002 | Brown |
| 6,524,231 B1 | 2/2003 | Westberg et al. |
| 6,551,512 B1 | 4/2003 | Britsch et al. |
| 6,652,476 B2 | 11/2003 | Langley et al. |
| 6,678,040 B1 | 1/2004 | Suzuki |
| 6,878,105 B2 | 4/2005 | Smith et al. |

APPARATUS FOR DETERMINING FLOW RATES OF BIOLOGICAL FLUIDS

This application is a divisional application of U.S. application Ser. No. 10/826,086, filed Apr. 16, 2004, now U.S. Pat. No. 7,087,177, issued on Aug. 8, 2006, which is hereby incorporated by reference herein.

The present invention relates in general to methods for separating biological fluids, such as blood, blood components or other biological fluids, into one or more components.

The separation of biological fluid such as whole blood, or blood components into its constituent components for various applications is well known. Many commercially available separation systems (commonly called "apheresis" systems) are based on principles of centrifugation, which separates the fluid components according to density. Various apheresis systems are known that employ centrifugal separation of blood or blood components including the CS-3000®, Amicus® and ALYX® separators marketed by Fenwal, Inc. of Lake Zurich, Illinois, the Spectra® and Trima® separators by Gambro BCT of Lakewood, Colo., the AS104 from Fresenius Homecare of Redmond, Wash., and the V-50 and other models from Haemonetics Corporation of Braintree, Mass.

Although the need may vary with application and components, available centrifugal blood processing systems employ various ways to collect the separated components from the centrifugal field with as little presence or contamination as possible from other components located in the centrifugal field. There is continuing desire to develop more efficient and versatile ways which minimize such presence or contamination during separation and collection of one or more blood components.

SUMMARY OF THE PRESENT INVENTION

In accordance with the present invention, apparatus and methods are provided for collecting and separating a biological fluid, such as whole blood, with improved efficiency and reduced presence or contamination by other components. In accordance with one aspect of the present invention, the apparatus comprises a processing chamber adapted for rotation about an axis. The apparatus includes an inlet to convey a first fluid into a chamber. The first fluid comprises first and second components having generally different densities such that an interface forms between at least portions of the first and second components at a first location during rotation of the chamber. The apparatus also includes at least one outlet to remove at least one of the first and second components of the first fluid from the chamber. The apparatus further comprises a controller adapted to introduce the first fluid into the chamber through the inlet and to remove the at least one of the first and second components through the outlet. The controller is operable to control the flow rates to move the interface from the first location to a second location and to move the interface from the second location in a direction toward the first location and to return the interface to the second location. The controller is operable to determine a flow rate of the first or second component within the first fluid in the channel, such determination being based, at least in part, on a time interval between when the interface moves between the second location to the first location and returns to the second location. The apparatus comprises at least one sensing assembly adapted to sense when the interface is at the first and second locations.

In an additional aspect of the present invention, the method includes introducing a first fluid comprising first and second components having generally different density into a centrifugal field and allowing an interface to form between at least portions of the first and second components at a first location. The method includes moving the interface from the first location to a second location. The method further includes introducing the first fluid and removing at least one of the first and second components at known controlled flow rates so as to move the interface from the second location in a direction toward the first location and to return the interface to the second location. The method further includes determining the flow rate of the first or second component within the first fluid where such determining is based, at least in part, on a time interval between when the interface moves from and returns to the second location.

Although the above apparatus and method may be used for a variety of biological fluid separation and collection procedures, they may be applied advantageously to whole blood. Employed in separation of blood, the first fluid may comprise whole blood. The first component may substantially comprise plasma and the second component may substantially comprise red blood cells. The interface is allowed to form at a first location with plasma and red blood cells being generally located at opposite sides of the interface. A portion of the plasma at one side of the interface may include substantial numbers of platelets, depending on the specific collection procedure.

In accordance with another aspect of the invention, the apparatus or method further comprises creating the centrifugal field about an axis of rotation which separates the components into different density. The interface formed between portions of the first and second components of the first fluid occurs at the first radial location relative to the axis of rotation. Where the first fluid comprises whole blood, lower density plasma is generally disposed at the radially inner side of the interface and red blood cells are generally disposed at the radially outer side of the interface. One or more intermediate density components, such as white cells and platelets, (which form what is commonly called the "buffy coat") may be disposed generally between the plasma and red blood cells. A significant concentration of platelets also may be suspended in the plasma for collection of plasma with a high concentration of platelets (commonly called "platelet rich plasma"), depending on the specific collection procedure.

Removal of one of the first and second components may include removing one component from the radially inner side of the interface when the interface is located at the second location. The second location is preferably defined by a component removable passage for removing one of the first and second components from the centrifugal field. Where the first fluid comprises whole blood, at least a portion of plasma may be removed from the radially inner side of the interface through a plasma component removal passage so as to determine the flow rate of plasma which is entering the centrifugal field. Removal of plasma may stop when the system detects a certain concentration of non-plasma components in the removal passage. A further modification may include returning a portion of plasma to the centrifugal field to minimize the concentration of undesired components in the plasma collected. The present invention may also be employed to determine the flow rate of red blood cells by removal of red blood cells at a known controlled flow rate through a corresponding red blood cell removal passage.

In accordance with a further aspect of the present invention, the apparatus or method may be employed for determining the flow rate of a selected component by measuring the weight of such component which has been removed from the centrifugal field during the above-mentioned time interval associated with the interface movement. When the first fluid comprises whole blood, the flow rate of the plasma may be determined by the weight of the plasma which is removed and collected during the time interval. Other components may be removed for collection and their weights measured so as to determine other flow rates, depending upon the specific procedure employed. By way of example and not limitation, the apparatus or method may be used to determine the red blood cell flow rate based on the weight of red blood cells removed during the appropriate time interval.

In a yet further aspect of the present invention, the interface may be moved from the second location to the first location by modifying the rate of removal of one of the first and second components. For example, the interface between plasma and red blood cells may be moved from the second location to the first location by reducing the removal rate of plasma from the centrifugal field. The rate of removal may be reduced to substantially zero although other reduced rates may also be used.

The interface may be returned to the second location by increasing the rate of removal of one of the first and second components, such as plasma, to a known controlled flow rate. In addition to the time interval described above, the determination of the flow rate of the first and second components may also be based, at least in part, on a time interval, which is measured between when the interface moves from the first location to when the interface returns to the second location, which time interval is a subset of the previously discussed or first time interval.

DETAILED DESCRIPTION

The present invention is described herein in the context of the Fenwal ALYX® Blood Collection and Separation System. The present invention is not, however, limited to a particular system or to a system made by a particular manufacturer. It may be employed in connection with or used in any of the blood collection and separation systems now available or that may yet be developed and used for a variety of blood or other biological fluid processing procedures. While the present invention will be described in connection with a human whole blood collection and separation procedure, it is contemplated that the present invention is not limited to whole blood or human blood and, in fact, may be employed with other biological fluids as well.

Figure 1:
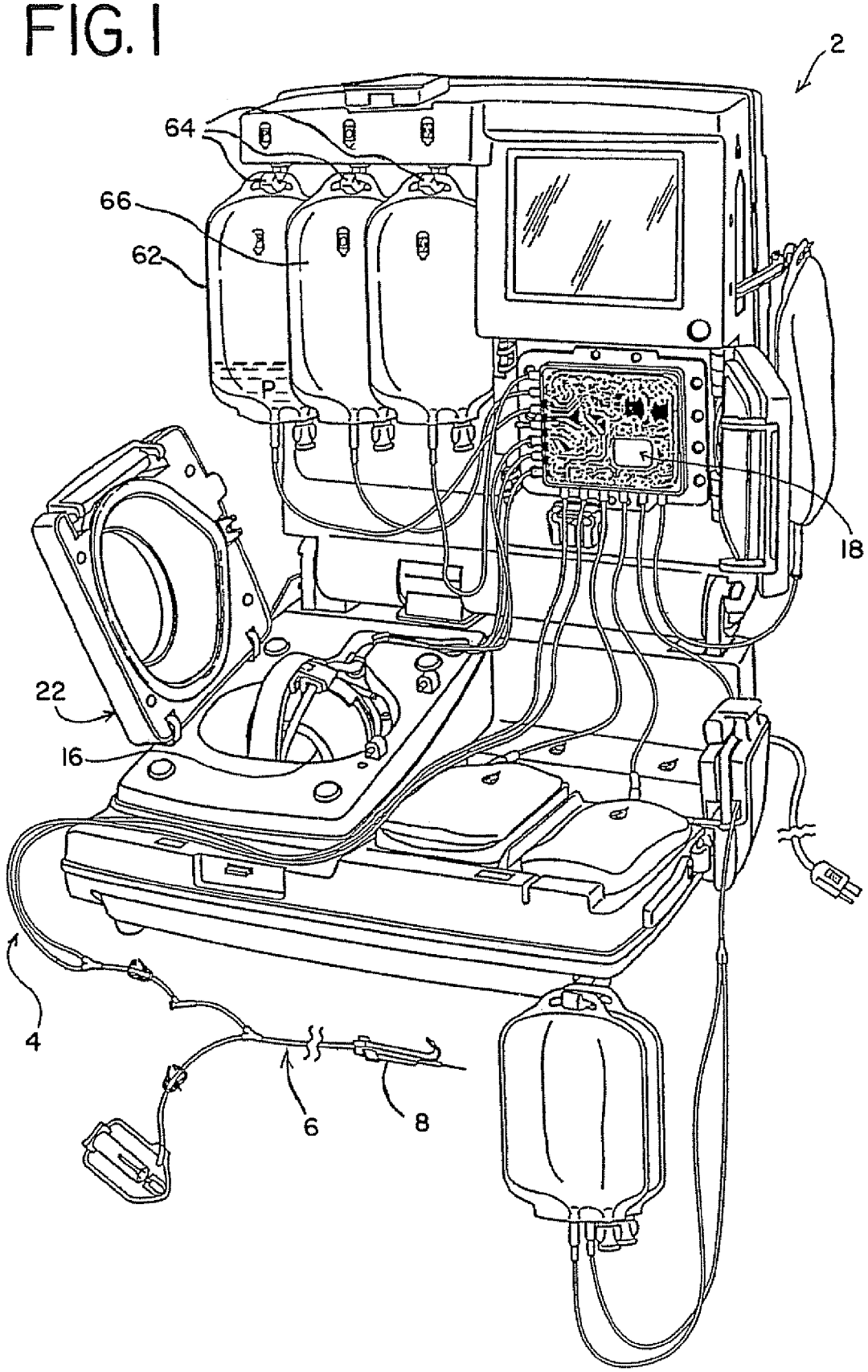
FIG. 1 is a perspective view of a combination reusable blood separation controller or control module and disposable fluid circuit assembly which has been loaded on to the reusable controller or control module and which may be employed in connection with the present invention.

As shown in FIG. 1, the system includes a reusable controller or control module 2 for carrying out a blood separation process in cooperation with a pre-sterilized and preferably, but not necessarily, integral, pre-assembled and disposable fluid circuit assembly, generally at 4. The reusable controller or control module and disposable circuit assembly are described in greater detail in one or more of the following patents or patent applications, each of which is hereby incorporated by reference into this description: U.S. Pat. No. 6,325,775, Published PCT Application Nos. PCT/US02/31317; PCT/US02/31319; PCT/US03/33311 and PCT/US03/07944, and U.S. Published Patent Application Nos. 20020094927 and 20020077241.

As noted earlier, the present invention may also be employed with other apheresis systems, such as the Amicus® separator shown in U.S. Pat. No. 5,370,802, hereby incorporated by reference herein, as well as the Haemonetics V-50 separator, Gambro Spectra® and Trima® separators and others as mentioned earlier.

As seen in FIG. 1, the disposable fluid circuit assembly 4 includes a fluid path, generally at 6, in the form of flexible plastic tubing terminating in a needle 8 for accessing a blood source, such as a blood vessel of a human subject. In many, perhaps most, applications, the blood source will be a human subject and more typically will be a healthy donor contributing blood for later administration to a patient requiring one or more blood components. However, unless specified in the claims, the present invention is not limited to use with a particular whole blood source or to a healthy donor. The fluid flow path continues from the needle, through the fluid circuit and into other, downstream components of the fluid circuit, for processing to separate the collected blood into one or more blood components, such as red cells, platelets, and plasma.

Control of the fluid within the tubing to the various chambers and structures may be controlled by a valving station 18 and/or by one or more clamps. Such valving station and clamps may, in turn, be controlled by the user, by a computer processing unit and associated software within the control module 2, or some combination of the two.

Figure 2:
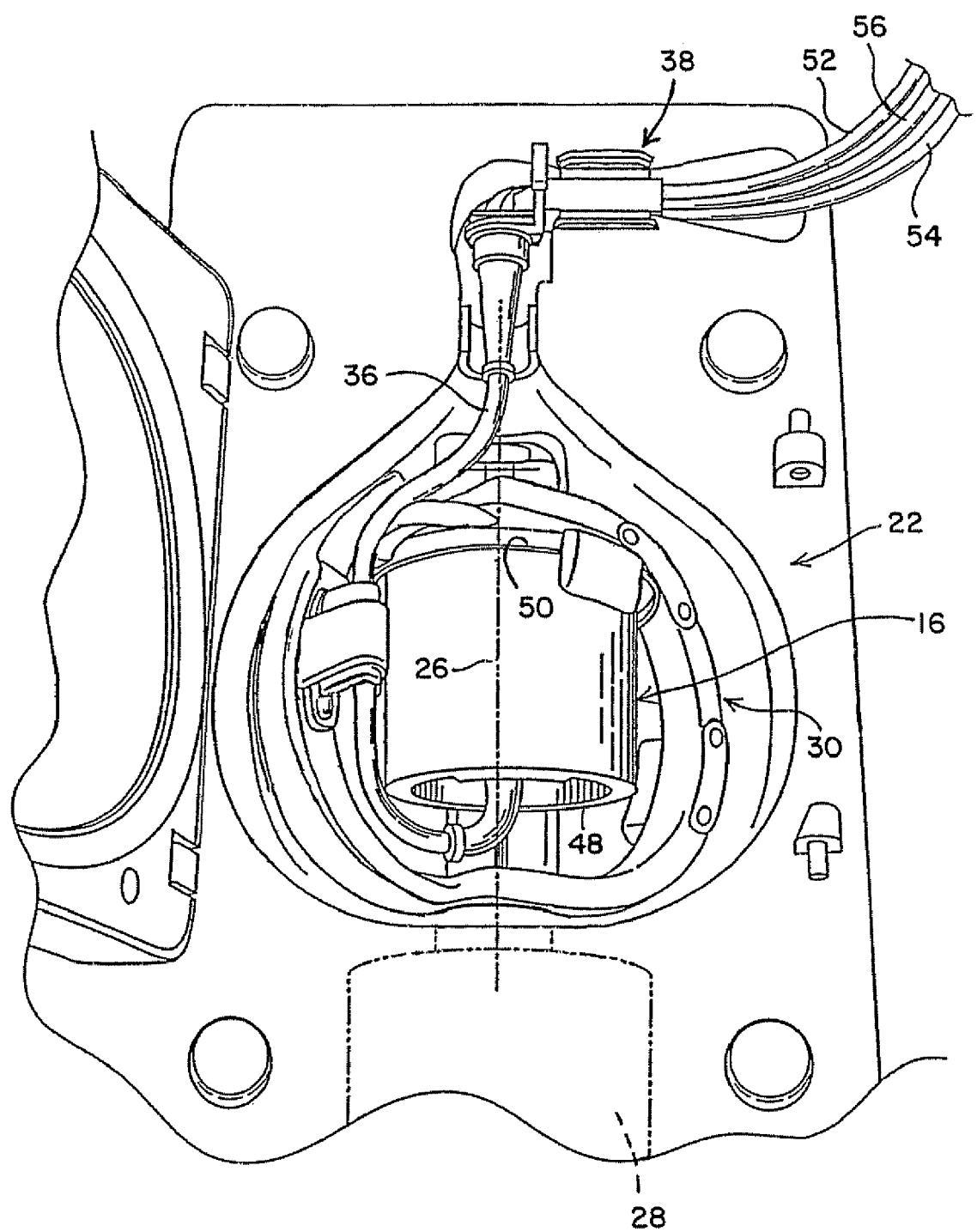
FIG. 2 is a perspective view of the interior of a centrifugal station shown in FIG. 1 after the disposable fluid circuit assembly has been loaded for use.

In FIG. 2, a processing chamber 16 is housed in an enclosure, generally indicated at 22, of the control module 2. Preferably, the centrifugal field is created by rotation of the chamber 16 about an axis 26. Such rotation may be supplied by a rotor 28 which spins a frame 30 about the axis 26. The rotor 28 is capable of rotating the frame 30 in either a clockwise or counterclockwise direction, depending upon the commands issued by the control module 2.

Figure 3:
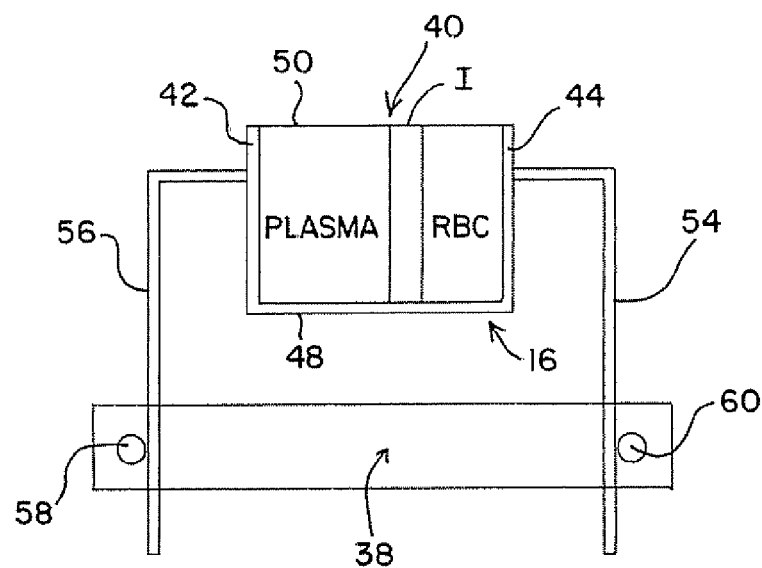
FIG. 3 is a diagrammatic view of the interior of the blood processing chamber of a type shown in FIGS. 1 and 2, showing the separation of whole blood into a red blood cell layer, a plasma layer, and an intermediate buffy coat layer, with the position of the layers shown during normal conditions.
Figure 4:
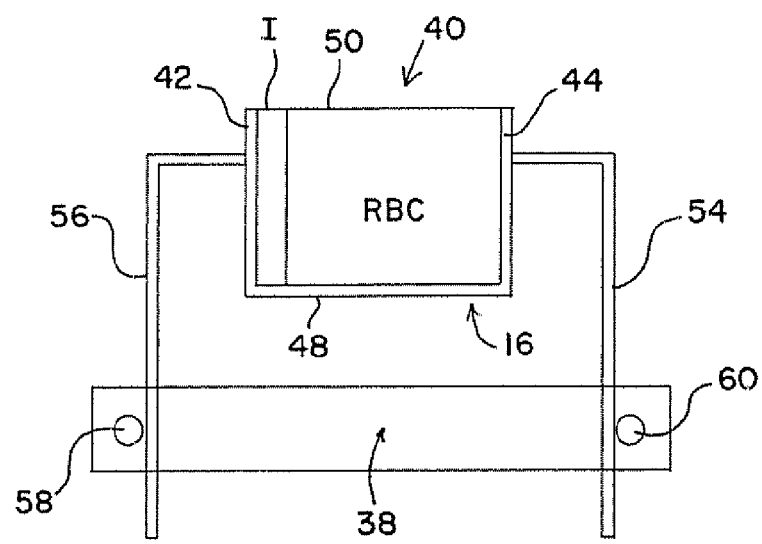
FIG. 4 is a diagrammatic view of the interior of the blood processing chamber of a type shown in FIGS. 1 and 2, with at least one of the buffy coat layer and the red blood cell layer having moved very close to the low-G wall.
Figure 5:
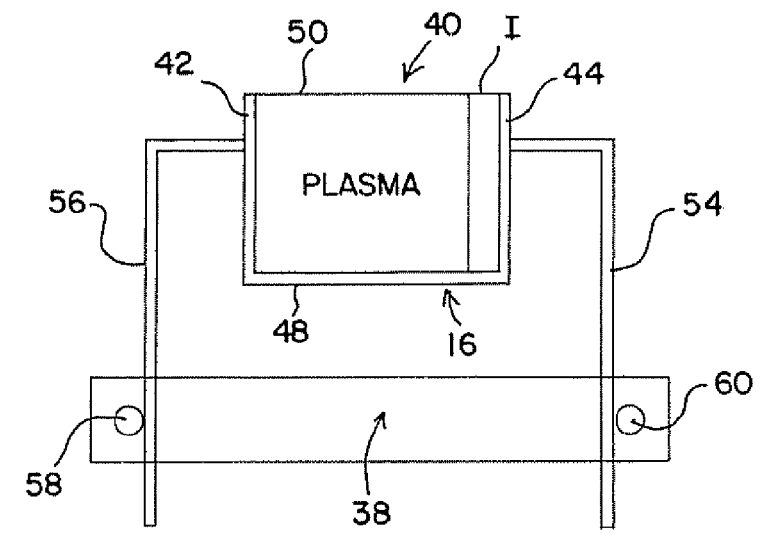
FIG. 5 is a diagrammatic view of the interior of the blood processing chamber of the type shown in FIGS. 1 and 2, with at least one of the buffy coat layer and the plasma layer having moved very close to the high-G wall.

As shown schematically in FIGS. 3-5, the processing chamber 16 generally defines a separation channel, generally at 40, which is disposed generally annularly about the axis 26 (FIG. 2). Such channel 40 is defined between a radially inner or low-G wall portion 42 and a radially outer or high-G wall portion 44, as shown in FIGS. 3-5. The channel 40 is also defined between opposing end wall portions 48 and 50, as shown in FIG. 2, at the top and bottom of the chamber 16. As used herein, the terms "top" or "bottom" are intended for the purpose of facilitating description of the present invention and are not intended to limit the position or arrangement of the chamber.

It also should be understood that the present invention may be employed in centrifugal structures other than those shown. For example, a separation channel may comprise a reusable platen, bowl or rotor into which a disposable flexible, rigid or semi-rigid liner is placed so that blood flows through the liner and does not contact the reusable portion. In such case, the configuration of the channel platen, bowl, frame or rotor defines the shape of fluid flow path and the disposable liner assumes a corresponding shape during operation. Examples of such may be seen in the CS-3000®, Amicus® and Spectra® centrifugal separation systems. Alternatively, the separation channel may be entirely disposable. For example, the channel may be formed of rigid plastic having a pre-formed shape through which the blood or other biological fluid is processed. Of course, the channel could be entirely reusable, in which case it would need to be cleaned and possibly sterilized between uses—an inconvenient and time consuming procedure. As such, it should be understood that the methods described and claimed are intended to have a broad interpretation that includes all of the more specific structures, such as those mentioned in U.S. Provisional Patent Application No. 60/533,820, filed Dec. 31, 2003 (hereby incorporated by reference), in which it may find commercial application.

Turning back to FIG. 2, the channel 40 is in fluid communication with the tubing assembly or umbilicus 36. The tubing assembly includes an inlet tube or passage 52 and two (or more) removal passages 54 and 56. When whole blood is being processed, the inlet tube 52 preferably carries anticoagulated whole blood into the channel 40 for separation. The removal tubing or passages 54 and 56 may, respectively, carry red blood cells and plasma from the channel 40, although this will depend on the particular collection procedure employed.

Figure 6:
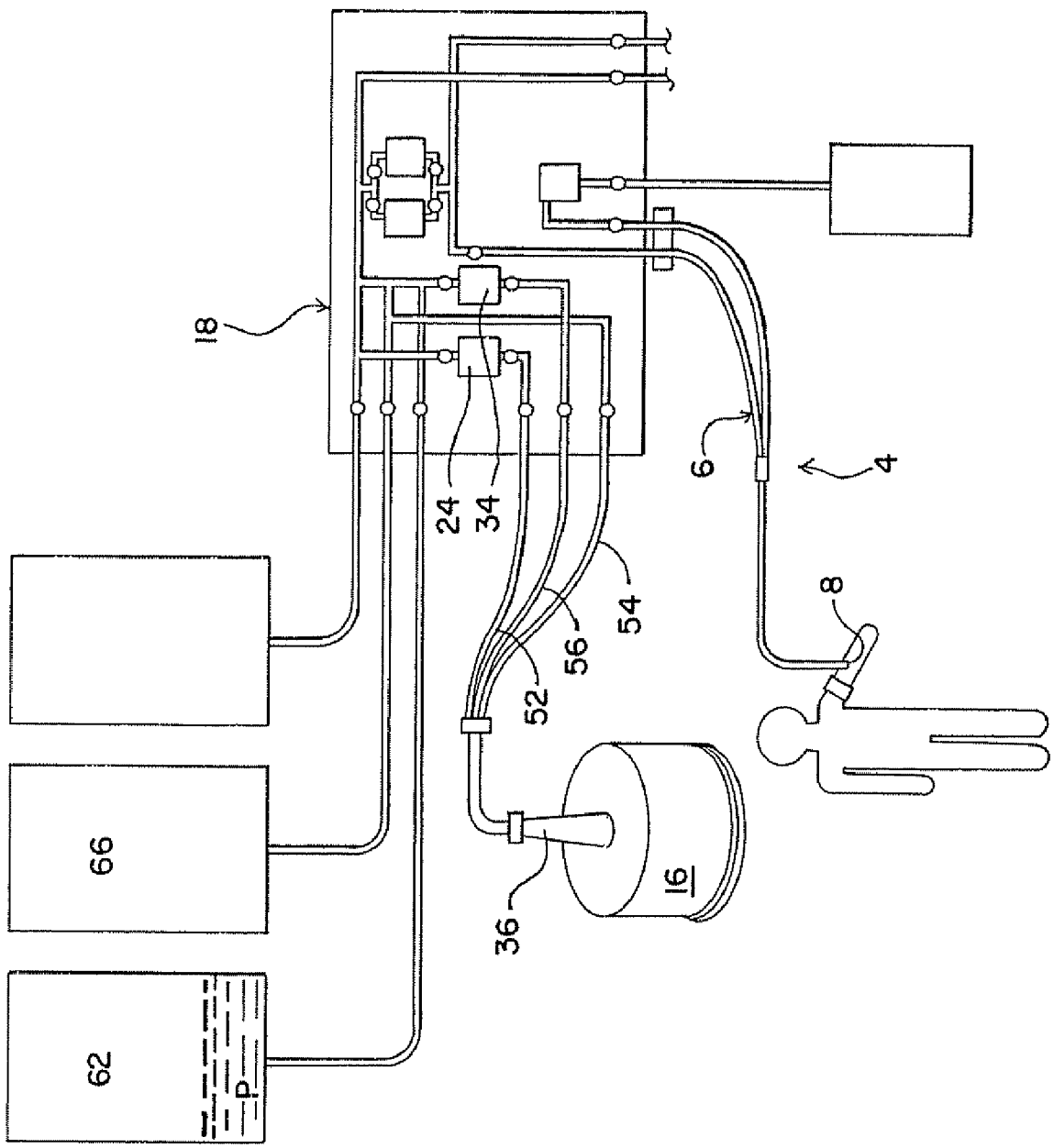
FIG. 6 is a schematic view of a fluid circuit assembly that can be implemented in accordance with the present invention.

Referring briefly to FIG. 6, whole blood may be collected from a blood source, anticoagulant added if needed, and directed into the centrifugal processing chamber 16. Introduction of the whole blood may be controlled by an in-process or whole blood pump 24, as shown in FIG. 6. The pump 24 preferably introduces the blood into the processing chamber (which is within the centrifugal field when rotated about an axis 26) at a known controlled flow rate. One or more pumps may control removal of one or more blood components, such as plasma, from the processing chamber. In FIG. 6, a plasma pump 34 provides for removal of plasma from the processing chamber at a known controlled flow rate through the plasma removal tubing 56.

In the processing chamber within the centrifugal field, the whole blood is allowed to separate based on density of its constituent components. The lower density components may generally, although not exclusively, be located nearer the radially inner or low-G wall portion while the higher density components may generally, although not exclusively, be located nearer the radially outer or high-G wall portion.

Turning back to FIGS. 3-5, in FIG. 3, a region or layer of plasma is disposed adjacent the inner or low-g wall portion 42 and a region or layer of red blood cells RBC is disposed adjacent the outer or high-G wall portion 44. An intermediate region or layer forms an interface I between the red blood cell region and the plasma region. The interface I generally may be populated by at least a portion of intermediate density cellular blood components like platelets and leukocytes (white cells), arranged according to density, with the platelets being generally closer to the plasma layer than the leukocytes, although the actual concentration of components present at the interface I between the plasma and the red blood cells will depend on the particular structures, rotational speeds and procedures employed. By way of example, and not limitation, a substantial concentration of platelets may be disposed just radially inward or above the interface so as to form a platelet rich plasma layer.

In accordance with the illustrated embodiment of the present invention, it is desirable to determine the volumetric or mass flow rate of at least one of the separated blood components as it is introduced (as part of the whole blood) into the centrifugal processing chamber 16. For example, the present invention in one aspect allows determination of the flow rate of plasma which is introduced (as part of the whole blood) into the centrifugal processing chamber 16. The flow rate of one or more blood components or a combination of such components may also be determined, depending on the specific procedure employed by the control module 2.

In accordance with the present invention, the determination of the flow rate of a component is preferably achieved, in part, by monitoring the location of the interface I. As seen in FIGS. 3-5, the interface I may be monitored by an optical sensing station 38 (see also FIG. 2). FIG. 3 generally shows a first location of the interface I, which location preferably has a radial position which is intermediate the radially inner and outer wall portions 42 and 44. In its broadest sense, the interface is monitored for location at a first position or first location which may be defined by any position of the interface which does not result in under spill or over spill conditions, which conditions will be described below.

The interface resistance is monitored by the optical sensing station 38, which includes first and second sensing assemblies 58 and 60. The first sensing assembly 58 in the station 38 optically monitors the passage of blood components through the plasma removal passage 56. The second sensing assembly 60 in the station 38 optically monitors the passage of blood components through the red blood cell removal passage 54.

The first sensing assembly 58 is capable of detecting the presence of optically targeted cellular components in the plasma removal passage 56. The presence or concentration of cellular components is empirically determined based on optical light transmission through a transparent section of the removal passage 56. The components that are optically targeted for detection vary, depending upon the procedure. By way of example and not limitation, the first sensing assembly 58 may be configured to detect the presence of platelets in the plasma. Alternatively, the sensing assembly 58 may be configured to detect the presence of other blood components in a blood mixture such as leukocytes or red blood cells in a mixture comprised of concentrated platelets in plasma.

In FIG. 4, the interface I is disposed at a radially inward or second location as compared to the first location of the interface in FIG. 3. In FIG. 4, the interface I is close enough to the low-G wall portion 56 of the channel 40 to allow at least a portion of the interface components, or red blood cells from the other side of the interface, or a combination thereof, to flow out of the channel 40 through the removal passage 56. Such components are detected by the sensing assembly 58 which communicates with other parts of the control module 2 to trigger a condition which will be called an "over spill."

By "over spill" condition, it is meant that a least of portion of the interface has moved radially inward sufficiently to pass into the plasma removal tubing or passage 56 so that a concentration of components which populate the interface or components which populate the other side of the interface are detected by the sensing assembly 58. The type and concentration of blood component which is sufficient to create an "over spill" may correspond to a predetermined threshold set by the control module 2 and will depend on the specific procedures employed by the control module 2. When the sensing assembly 58 optically detects such concentration, an over spill condition is registered by the control module 2.

In FIG. 5, the radial position of the interface is located radially outward to an alternate second location as compared to the first location of the interface in FIG. 3. A second sensing assembly 60 in the removal passage 54 detects that a portion of the plasma or interface components are exiting the tube 54, which otherwise usually has concentrated red blood cells exiting therethrough. This condition is commonly called an "under spill" condition. When the presence of sufficient blood components other than red blood cells are detected by the sensing assembly 60 in the removal passage 54, the control module 2 preferably triggers an under spill condition. Depending on the particular chamber structure and procedures employed, platelets which populate the interface may or may not be spilled out of the chamber during an under spill condition.

In accordance with the present invention, the interface is intentionally moved from the first location, such as that shown in FIG. 3 to the second location, such as either of those shown in FIG. 4 or 5. The direction of radial movement of the interface will generally depend on which introductory flow rate is to be determined. The interface will preferably be moved radially inward, such as shown in FIG. 4, where it is desired to determine the inlet flow rate of plasma (within the whole blood being introduced). Where it is desired to determine the inlet flow rate of red blood cells in the whole blood, the interface will preferably be moved radially outward, such as shown in FIG. 5.

The interface may be moved to the second location (shown in FIG. 4), by controlling the flow rate of one or more of the in-process pump 24 or the plasma pump 34, and/or controlling the centrifuge speed. For example, the plasma pump 34 may be operated at a flow rate ($Q_0$) which is greater than the flow rate of plasma in the channel 40. Such flow rate is preferably sufficient to move the interface radially inward to the second location so that the sensing assembly 58 detects an over spill condition.

When an over spill condition is detected by the sensing assembly 58, the rate of removal of the plasma is preferably reduced. The rate of removal of plasma may be reduced by decreasing the flow rate of at least one of or both pumps 24 and 34. For example, the plasma pump 34 may be decreased to a known controlled flow rate ($Q_1$) so as to reduce the rate of removal of plasma and other blood components through the removal passage 56. Such reduced flow rate ($Q_1$) may be reduced to nearly zero or may be stopped altogether, if desired.

The reduced flow rate ($Q_1$) is maintained for a certain interval of time and preferably allows the interface to move radially outward or return to a location such as the first location in FIG. 3. The time during which the rate of removal is reduced or stopped may be a predetermined time period set ($T_1$) by the control module 2. After such time interval ($T_1$) has elapsed, the rate of removal of blood components through the removal passage 56 is increased or restarted.

The increased or resumed flow rate ($Q_2$) is preferably sufficient to move the interface from the intermediate or first location in FIG. 3 and return the interface to the second location in FIG. 4 to cause another or second over spill condition. The time interval ($T_2$) from the beginning of the increased or resumed flow until the interface returns to the second location in FIG. 4 and spills over again may also be measured.

A total time ($T_s$) may also be measured between the first and second over spill conditions. This total time ($T_s$) is also comprised of the sum of the previously described time intervals ($T_1$) and ($T_2$) which measure the time the interface is first moved from the second location to the first location and the time the interface returns from the first location to the second location. The flow rate of plasma introduced into the chamber, as part of the whole blood, ($Q_P$) may be determined based on the following equation: $Q_P=(Q_2*T_2)/(T_s)$. Such plasma flow rate may be calculated by the control module 2, if desired, and may be determined one or more times during the collection procedure.

In one aspect of the present invention, the method is based on the assumption that the radial location of the interface at two successive spills will be approximately the same. The interface will move down some unknown radial distance, d, during the period in which the plasma pump 34 is not operating and must move back that same distance while the plasma pump is operating in order to trigger the next spill. The radial distance may be represented as $d=(Q_{TP}*t_1)/$(chamber area) during the no-pump period and $d=(Q_P-Q_{TP})*t_2/$(chamber area) during the period in which the plasma pump is operating. The term ($t_1+t_2$) is also equal to the total time between spills, $t_S$, so the equation is presented as $Q_{TP}=(Q_P*t_2)/t_S$. Thus, to calculate the flow rate of plasma introduced into the chamber, as part of the whole blood, one only needs to know the plasma pump rate and any two of the following three time periods: no-pump time; pumping time; and time between spills.

The algorithm becomes particularly easy if all the plasma pumped processed during the period of time between spills is sequestered in a container coupled to a weight scale. Since the quantity ($Q_P*t_2$) is just the total volume of plasma collected between spills, the equation reduces to simply $Q_{TP}=(\Delta W_P)/(\square_P*t_S)$ where $\Delta W_P$ is the weight change of the plasma container and $\square_P$ is the density of plasma (about 1.025). The approach is especially useful since it does not require that the plasma pump rate be either known or constant.

In this regard, another aspect of the present invention allows the plasma flow rate to be determined based on the weight of plasma $\square_P$ which is collected during the time period between over spill conditions ($T_s$). As shown in FIGS. 1 and 6, the plasma P which is removed from the channel 40 between the over spill conditions is preferably sequestered in a plasma collection container 62. The weight of sequestered plasma ($W_P$) may be monitored by a weight scale or sensor 64 (FIG. 1). If the plasma collection container 62 already contains a certain amount of plasma due to collection commenced prior to the measured time period ($T_s$), then the weight change of plasma ($\Delta W_P$) in the plasma collection container 62 during the time period ($T_s$) is monitored.

It may be advantageous to determine the flow rate of a particular blood component within the centrifugal field for several reasons. For example, plasma may be removed and collected from one side of the interface at a rate which is substantially equal to the rate at which it is introduced with the whole blood which is introduced into the centrifugal field. Collecting plasma at this rate may result in collected plasma which has a lower concentration of other unwanted blood components from the other side of the interface or from blood components which populate the interface itself.

Alternatively, the flow rates of other blood components or combinations of blood components may be determined such as for example, red blood cells and platelet rich plasma. The flow rate of red blood cells may be determined in a similar manner to that described above except that the interface moves from and to the alternate second location (under spill condition), similar to that shown in FIG. 5, which location is radially outward of the first location in FIG. 3. As shown in FIGS. 1 and 6, the red blood cells collected during the total time between spills may be stored in an appropriate red blood cell collection container 66 which is attached to a respective weighing sensor 64.

The present invention also allows the flow rate of a particular blood component or combination thereof to be determined one or more times during the collection procedure, if desired.

If more than one collection procedure is employed, the present invention may be repeated as many times as desired.

Other modifications are also possible. Any of the above methods may be modified so that a portion of the blood components which are removed from the centrifugal field during the over spill or under spill conditions are returned to the centrifugal field, if desired. For example, a portion of the plasma which is collected in the plasma container 62 may be returned following an over spill condition, if desired. Because such plasma may contain undesired components such as, from the other side of the interface, such as red blood cells or leukocytes which populate the interface. Therefore, the return of such portion to the centrifugal field may minimize the concentration of such other components in the collected plasma. In a similar manner, a portion of the red blood cells which are collected in the red blood cell container 66 during an under spill condition may be returned to the centrifugal field, if desired.

As can be seen from the above description, the present invention has several different aspects and features, which are not limited to the specific procedures discussed or the specific structures shown in the attached drawings. Variations of these features may be embodied in other procedures and structures for carrying out other procedures for blood separation, processing or collection.

The invention claimed is:

1. An apparatus comprising:
a processing chamber adapted for rotation about an axis;
an inlet to convey a first fluid into the chamber, the first fluid comprising first and second components having generally different densities such that an interface forms between at least portions of the first and second components at a first location during rotation of the chamber;
at least one outlet to remove at least one of the first and second components of the first fluid from the chamber;
a controller adapted to introduce the first fluid to the chamber through the inlet at a rate of introduction and to remove at least one of the first and second components through the outlet at a rate of removal, the controller being operable to control the rates of introduction and/or removal to move the interface from the first location to a second location and to move the interface from the second location in a direction toward the first location and to return the interface to the second location,
the controller being operable to determine a flow rate of the first or second component within the first fluid in the chamber, such determination being based, at least in part, on a time interval between when the interface moves between the second location to the first location and returns to the second location; and
at least one sensing assembly adapted to sense when the interface is at the first and second locations.

2. The apparatus of claim 1 wherein the controller determines the weight of one component removed during the time interval.

3. The apparatus of claim 1 wherein the outlet is adapted for removal of one component from the radially inner side of the interface.

4. The apparatus of claim 1 wherein the outlet is adapted for removal of one component from the radially outer side of the interface.

5. The apparatus of claim 1 wherein the second location is defined by a component removal passage for removing one of the first and second components.

6. The apparatus of claim 1 wherein the controller is operable to move the interface from the second location to the first location by reducing the rate of removal of the one of the first and second components.

7. The apparatus of claim 6 in which the rate of removal is substantially zero.

8. The apparatus of claim 1 wherein the controller is operable to move the interface to the second location by increasing the rate of removal of one of the first and second components to a known controlled flow rate.

9. The apparatus of claim 1 wherein the controller is operable to determine the flow rate based, at least in part, on known controlled rates of introduction and removal employed during moving the interface from and returning to the second location.

10. The apparatus of claim 1 wherein the controller is operable to determine the flow rate based on the first named time interval and a second time interval which is measured between when the interface moves from the first location and returns to the second location.

* * * * *

UNITED STATES PATENT AND TRADEMARK OFFICE
CERTIFICATE OF CORRECTION

PATENT NO. : 7,396,452 B2 Page 1 of 1
APPLICATION NO. : 11/427402
DATED : June 29, 2006
INVENTOR(S) : Kyungyoon Min and Richard I. Brown It is certified that error appears in the above-identified patent and that said Letters Patent is hereby corrected as shown below:

Claim 8, Line 32, change "controlled flow rate." to -- controlled rate. --.

Signed and Sealed this

Twenty-first Day of October, 2008

JON W. DUDAS
*Director of the United States Patent and Trademark Office*

UNITED STATES PATENT AND TRADEMARK OFFICE
CERTIFICATE OF CORRECTION

PATENT NO.         : 7,396,452 B2                                          Page 1 of 1
APPLICATION NO.    : 11/427402
DATED              : June 29, 2006
INVENTOR(S)        : Kyungyoon Min and Richard I. Brown It is certified that error appears in the above-identified patent and that said Letters Patent is hereby corrected as shown below:

Column 10, Claim 8, Line 32, change "controlled flow rate." to -- controlled rate. --.

This certificate supersedes the Certificate of Correction issued October 21, 2008.

Signed and Sealed this

Eleventh Day of November, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,396,452 B2 |
| APPLICATION NO. | : 11/427402 |
| DATED | : July 8, 2008 |
| INVENTOR(S) | : Kyungyoon Min and Richard I. Brown |

It is certified that error appears in the above-identified patent and that said Letters Patent is hereby corrected as shown below:

Column 10, Claim 8, Line 32, change "controlled flow rate." to -- controlled rate. --.

This certificate supersedes the Certificates of Correction issued October 21, 2008 and November 11, 2008.

Signed and Sealed this

Ninth Day of December, 2008

JON W. DUDAS
*Director of the United States Patent and Trademark Office*